US009839400B2

(12) United States Patent
Oishi (10) Patent No.: US 9,839,400 B2
(45) Date of Patent: Dec. 12, 2017

(54) X-RAY CT APPARATUS INCLUDING AIR INLET AND AIR OUTLET CONNECTED BY A PATH INCLUDING A CONTROLLER

(71) Applicant: Toshiba Medical Systems Corporation, Otawara-shi (JP)

(72) Inventor: Keisuke Oishi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/701,585

(22) Filed: May 1, 2015

(65) Prior Publication Data
US 2015/0320376 A1     Nov. 12, 2015

(30) Foreign Application Priority Data

May 9, 2014   (JP) .................................. 2014-097962

(51) Int. Cl.
*H01J 35/10*       (2006.01)
*A61B 6/03*        (2006.01)
*A61B 6/00*        (2006.01)

(52) U.S. Cl.
CPC .............. *A61B 6/032* (2013.01); *A61B 6/035* (2013.01); *A61B 6/4405* (2013.01); *A61B 6/4488* (2013.01)

(58) Field of Classification Search
CPC .. A61B 6/00; A61B 6/02; A61B 6/022; A61B 6/025; A61B 6/027; A61B 6/032; A61B 6/045; A61B 6/44; A61B 6/4405; A61B 6/4411; A61B 6/4429; A61B 6/4435; A61B 6/4441; A61B 6/4447; A61B 6/4452; A61B 6/4458; A61B 6/4464; A61B 6/447; A61B 6/4488
USPC ........................................................ 378/199
See application file for complete search history.

(56) References Cited

U.S. PATENT DOCUMENTS

| | | | | |
|---|---|---|---|---|
| 2005/0041772 | A1* | 2/2005 | Nishide ................. | A61B 6/032 378/19 |
| 2005/0207530 | A1* | 9/2005 | Inoue .................... | A61B 6/032 378/63 |
| 2009/0041181 | A1* | 2/2009 | Krug .................... | A61B 6/035 378/19 |
| 2010/0172468 | A1* | 7/2010 | Gregerson ........... | A61B 5/0555 378/20 |
| 2011/0228910 | A1* | 9/2011 | Gregerson ........... | A61B 6/4488 378/200 |

FOREIGN PATENT DOCUMENTS

| | | |
|---|---|---|
| JP | 07-148147 | 6/1995 |
| JP | 2004-195224 | 7/2004 |
| JP | 2008-164548 | 7/2008 |
| JP | 2013-169396 | 9/2013 |

* cited by examiner

*Primary Examiner* — Jason McCormack
(74) *Attorney, Agent, or Firm* — Oblon, McClelland, Maier & Neustadt, L.L.P.

(57) ABSTRACT

An X-ray CT apparatus according to an embodiment includes a gantry, an air inlet, and an air outlet. The gantry supports an X-ray tube and an X-ray detector. The air inlet is provided in the gantry to draw air into the gantry from outside the gantry. The air outlet is provided in a lower section of the gantry to discharge air from the gantry through a path that houses a controller that controls the gantry.

18 Claims, 8 Drawing Sheets

000
X-RAY CT APPARATUS INCLUDING AIR INLET AND AIR OUTLET CONNECTED BY A PATH INCLUDING A CONTROLLER

CROSS-REFERENCE TO RELATED APPLICATION

This application is based upon and claims the benefit of priority from Japanese Patent Application No. 2014-097962, filed on May 9, 2014, the entire contents of all of which are incorporated herein by reference.

FIELD

Embodiments described herein relate generally to an X-ray CT apparatus.

BACKGROUND

In recent years, there have been cases where X-ray computed tomography (CT) devices capture a subject that is placed on a bed or an operating table of a different medical-image diagnostic apparatus. In such a case, an X-ray CT apparatus is moved on a rail so that it is moved to a position where it is possible to capture a subject that is placed on a bed or an operating table.

To discharge heat within a gantry in the above-described X-ray CT apparatus, for example, air is drawn from the side of a rail of the gantry, it is flowed to the ceiling surface of the gantry by a fan that is provided in an upper section of the gantry, and air is discharged out of the gantry from the ceiling surface of the gantry.

DETAILED DESCRIPTION

An explanation is given below, with reference to the drawings, of an X-ray computed tomography (CT) device according to an embodiment. Embodiments are not limited to the embodiments that are described below. Furthermore, the contents of the description of an embodiment are also applied to other embodiments in principle.

An X-ray CT apparatus according to an embodiment includes a gantry, an air inlet, and an air outlet. The gantry supports an X-ray tube and an X-ray detector. The air inlet is provided on the gantry to draw air into the gantry from outside the gantry. The air outlet is provided in a lower section of the gantry to discharge air within the gantry through a path that houses a controller that controls the gantry.

(First Embodiment)

Figure 1:
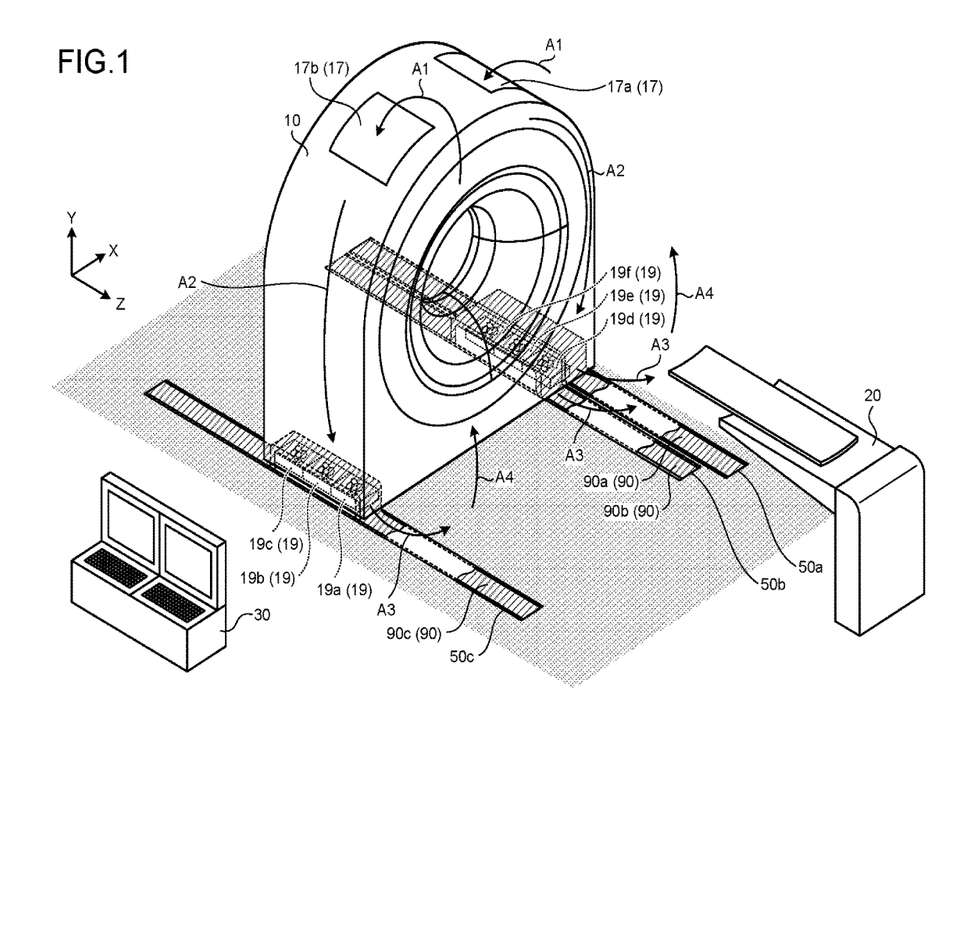
FIG. 1 is a perspective view that illustrates a configuration of an X-ray CT apparatus according to a first embodiment.

FIG. 1 is a perspective view that illustrates a configuration of an X-ray CT apparatus according to a first embodiment. As illustrated in FIG. 1, the X-ray CT apparatus according to the first embodiment includes a gantry 10, a bed 20, a console 30, a rail 50a, a rail 50b, and a rail 50c. Furthermore, the orthogonal coordinate system that is formed by the X axis, the Y axis, and the Z axis is defined as illustrated in FIG. 1. Specifically, the X axis represents a horizontal direction, the Y axis represents a vertical direction, and the Z axis represents a moving direction of the gantry 10. In the orthogonal coordinate system, the direction indicated by an arrow is a positive direction.

The gantry 10 emits X-rays to a subject P and acquires projection data from detection data on X-rays that are transmitted through the subject P. The bed 20 carries the subject P. An explanation is given below of a case where the bed 20 is fixedly attached to the floor surface; however, there is no limitation on the embodiment. For example, the bed 20 may be movable on the floor surface. The console 30 receives an operation on the X-ray CT apparatus by an operator and also reconstructs CT image data from projection data that is acquired by the gantry 10. Furthermore, the gantry 10 and the bed 20 are installed within a radiation controlled area, and the console 30 is installed outside a radiation controlled area.

The rail 50a, the rail 50b, and the rail 50c are the grooves that are provided on the floor surface, and they are the movement paths of the gantry 10. Here, the rail 50b is the driving rail that includes a driving mechanism, such as a ball screw, and the rail 50a and the rail 50c are the guide rails that support the movement of the gantry 10 in a traveling direction. In other words, the rail 50a and the rail 50c are the supporting mechanisms that support the movement of the gantry 10 in a traveling direction. Thus, the rail 50a, the rail 50b, and the rail 50c are the paths that house the controllers that control the gantry 10. The rail 50a, the rail 50b, and the rail 50c are referred to as a rail 50 if they are not distinguished from one another.

In the above-described X-ray CT apparatus, for example, the gantry 10 is driven by, for instance, a ball screw, and is moved on the rail 50 so that it is moved to a position where it is possible to capture the subject P that is placed on the bed 20. Then, the X-ray CT apparatus captures the subject P that is placed on the bed. Then, in order to ensure the space for a doctor to perform an operation, the gantry 10 is moved on the rail 50 so that it is moved to a position away from the bed 20. Then, a user, such as a doctor, determines a surgery site by using, for example, a medical image that is captured by the X-ray CT apparatus and performs an operation on the determined site. Furthermore, in some cases, after an operation is performed on the determined site by a doctor, capturing is performed on the surgery site. In such a case, the gantry 10 is moved on the rail 50 so that it is moved again to the position where the subject P placed on the bed 20 can be captured.

Figure 2:
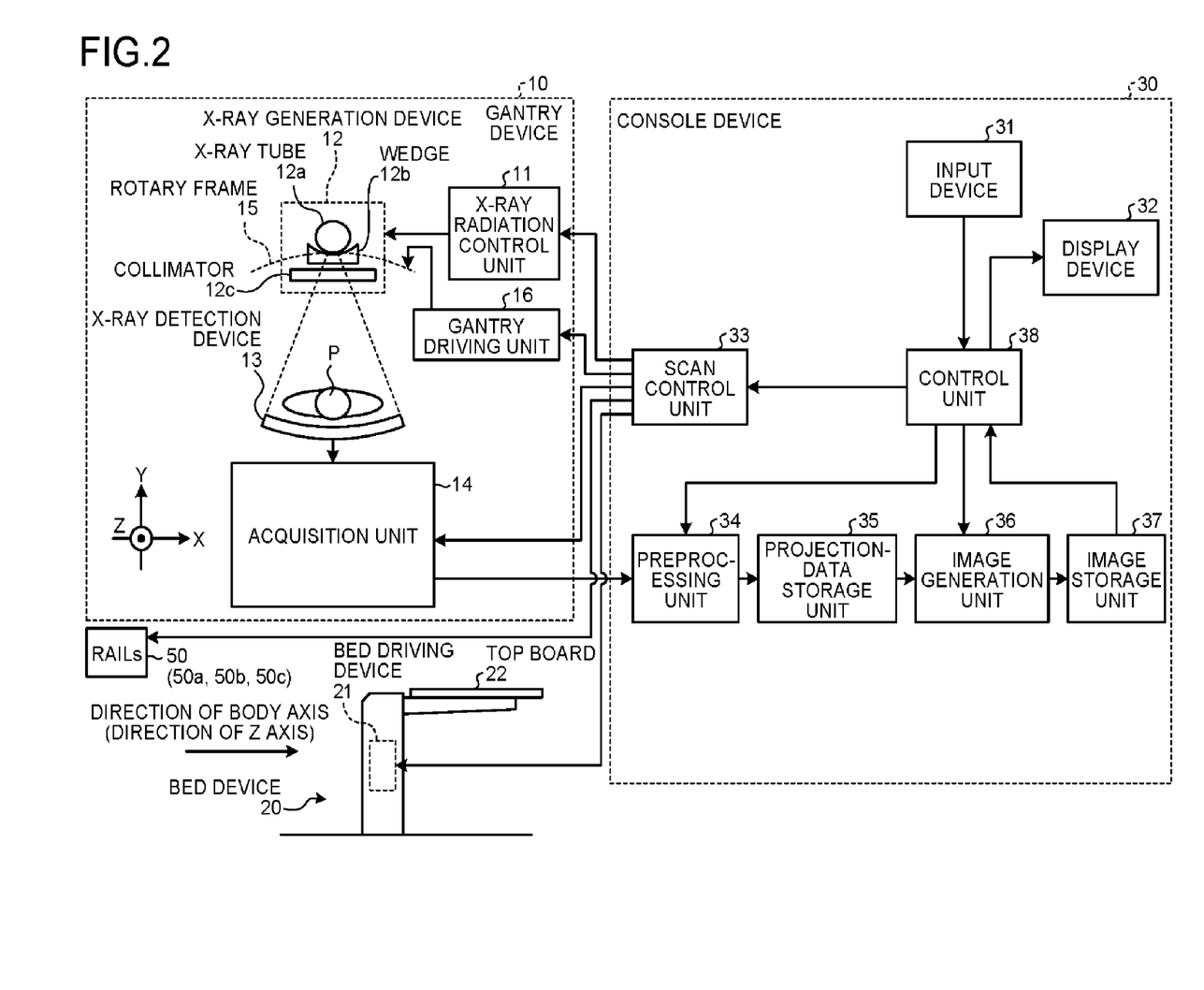
FIG. 2 is a functional block diagram that illustrates a functional configuration of the X-ray CT apparatus according to the first embodiment.

Next, an explanation is given of the functionality of each unit of the X-ray CT apparatus with reference to FIG. 2. FIG. 2 is a functional block diagram that illustrates the functional configuration of the X-ray CT apparatus according to the first embodiment. As illustrated in FIG. 2, the gantry 10 includes an X-ray radiation control unit 11, an X-ray generator 12, an X-ray detector 13, an acquisition unit 14, a rotary frame 15, and a gantry driving unit 16.

The rotary frame 15 rotatably supports the X-ray generator 12 and the X-ray detector 13 around the subject P. The rotary frame 15 supports the X-ray generator 12 and the X-ray detector 13 such that they are opposed to each other with the subject P interposed therebetween, and it is an annular frame that rotates at high speed in a circular orbit around the subject P by the gantry driving unit 16 that is described later.

The X-ray generator 12 is the device that generates X-rays and emits the generated X-rays to the subject P. The X-ray generator 12 includes an X-ray tube 12a, a wedge 12b, and a collimator 12c. The X-ray detector 13 detects X-rays that are emitted by the X-ray generator 12 and that are transmitted through the subject P. Specifically, the X-ray detector 13 uses X-ray detection elements that are arranged in two dimensions to detect X-rays that are emitted by the X-ray tube 12a and that are transmitted through the subject P.

The X-ray radiation control unit 11 is a unit that serves as a high-voltage generation unit and that supplies a high voltage to the X-ray tube 12a, and the X-ray tube 12a generates X-rays by using the high voltage that is supplied by the X-ray radiation control unit 11. The X-ray radiation control unit 11 adjusts the tube voltage or the tube current that is supplied to the X-ray tube 12a, thereby adjusting the amount of X-rays that are emitted to the subject P. Furthermore, the X-ray radiation control unit 11 adjusts the numerical aperture of the collimator 12c, thereby adjusting the radiation range (the fan angle or the cone angle) of X-rays. Under the control of the X-ray radiation control unit 11, the X-ray tube 12a is capable of continuously emitting X-rays all around the subject P for a full reconstruction or continuously emitting X-rays for a half reconstruction within an emission range (180°+ the fan angle) that enables a half reconstruction.

The gantry driving unit 16 drives and rotates the rotary frame 15 so that the X-ray generator 12 and the X-ray detector 13 are rotated in a circular orbit around the subject P.

The acquisition unit 14 is a data acquisition system (DAS), and it acquires projection data from detection data on X-rays that are detected by the X-ray detector 13.

The bed 20 is the device on which the subject P is placed, and it includes a top board 22 and a bed driving device 21. The top board 22 is the board on which the subject P is placed. The bed driving device 21 is capable of moving the top board 22 in a direction of the X axis or in a direction of the Y axis under the control of a scan control unit 33 that is described later.

The rails 50 (the rail 50a, the rail 50b, and the rail 50c) are the paths that house the controllers that control the gantry 10.

The console 30 includes an input device 31, a display device 32, the scan control unit 33, a preprocessing unit 34, a projection-data storage unit 35, an image generation unit 36, an image storage unit 37, and a control unit 38.

The input device 31 includes a mouse, keyboard, button, pedal (foot switch), or the like, that is used for inputting various instructions or various settings by an operator of the X-ray CT apparatus, and it transmits, to the control unit 38, information on the instructions or settings that are received from an operator.

The display device 32 is a monitor that an operator sees and, under the control of the control unit 38, it displays X-ray CT image data to an operator or displays a Graphical User Interface (GUI) for receiving various instructions, various settings, or the like, from an operator via the input device 31. For example, an operator uses the input device 31 to input, to an examination-information registration GUI, examination information, such as the body position of the subject P that is placed on the top board 22 during capturing.

Under the control of the control unit 38 that is described later, the scan control unit 33 controls the operations of the X-ray radiation control unit 11, the gantry driving unit 16, the acquisition unit 14, the bed driving device 21, and the driving mechanism of the rail 50b thereby controlling an operation to acquire projection data by the gantry 10.

The preprocessing unit 34 performs a correction operation, such as a logarithmic conversion operation, an offset correction, a sensitivity correction, or a beam hardening correction, on projection data that is generated by the acquisition unit 14, thereby generating corrected projection data.

The projection-data storage unit 35 stores the corrected projection data that is generated by the preprocessing unit 34. Furthermore, the projection-data storage unit 35 stores projection data that is acquired by the acquisition unit 14.

The image generation unit 36 is a processing unit that generates various types of image data by using projection data that is stored in the projection-data storage unit 35. The image storage unit 37 stores various types of image data that is generated by the image generation unit 36.

The control unit 38 controls operations of the gantry 10, the bed 20, and the console 30, thereby performing the overall control of the X-ray CT apparatus. Specifically, the control unit 38 controls the scan control unit 33 so as to control scanning that is performed by the gantry 10. Furthermore, the control unit 38 controls the preprocessing unit 34 or the image generation unit 36 so as to control an image reconstruction operation or an image generation operation by the console 30. Moreover, the control unit 38 performs a control so as to display, on the display device 32, various types of image data that is stored in the image storage unit 37.

Return to FIG. 1. Furthermore, a cooling unit is provided to discharge heat that is generated by the X-ray tube 12a to outside during capturing by the X-ray CT apparatus. For example, as illustrated in FIG. 1, air inlets 17a and 17b are provided in an upper section of the gantry 10. Here, "an upper section of the gantry 10" indicates a section that is above the central position in a height direction of the gantry 10, typically the ceiling surface or the side surface of the gantry 10. The gantry 10 draws air into the rotary frame 15 through the air inlet 17a and the air inlet 17b.

Furthermore, fans 19a to 19f are provided in a lower section of the gantry 10. Here, "a lower section of the gantry 10" indicates a section that is below the central position in a height direction of the gantry 10, typically the bottom surface of the gantry 10. An explanation is given based on the assumption that, after the power of the X-ray CT apparatus is turned on before the start of an examination, the power-on state is maintained all day in principle. Therefore, after the power of the gantry 10 is turned on, the fans 19a to 19f are continuously operating regardless of whether it is during capturing or not during capturing.

Furthermore, after the power of the gantry 10 is turned on, air within the rotary frame 15 is discharged out of the gantry 10 by the fans 19a to 19f of the gantry 10. That is, the fans 19a to 19f serve as exhaust fans. If the fans 19a to 19f are not distinguished from one another, they are sometimes referred to as a fan 19. Furthermore, in the example illustrated in FIG. 1, the three fans 19 are provided on the right and left sides; however, there is no limitation on the number of the fans 19 that are provided in the gantry 10, and it may be optionally changed.

Thus, the air flow illustrated in FIG. 1 is formed. Specifically, air is drawn through the air inlet 17a and the air inlet 17b into the rotary frame 15 (see A1). Then, in accordance with the rotation of the fans 19, the air that is drawn into the rotary frame 15 flows from the upper section of the rotary frame 15 to the lower section thereof (see A2). Then, the air that flows from the upper section of the rotary frame 15 is discharged out of the gantry 10 by the fans 19 (see A3). Here, an air outlet 40 is provided in a lower section of the gantry 10 on at least any one of the movement paths through which the gantry 10 moves. Thus, in the X-ray CT apparatus according to the first embodiment, air within the gantry 10 is discharged through the movement path that houses the controller that controls the gantry 10. The air that is discharged out of the gantry 10 is drawn again into the rotary frame through the air inlet 17a and the air inlet 17b (see A4).

Figure 3:
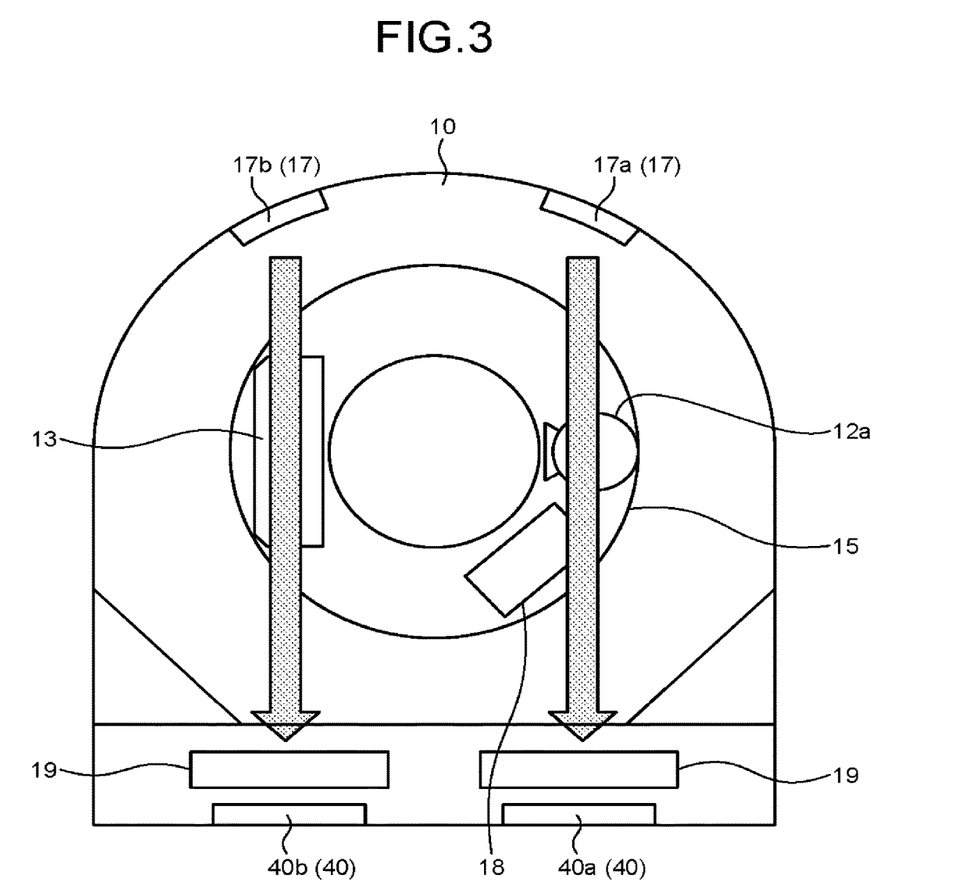
FIG. 3 is a diagram that illustrates an example of the location of each unit in a rotary frame according to the first embodiment.

Next, an explanation is given of the location of each component in the rotary frame 15 with reference to FIG. 3. FIG. 3 is a diagram that illustrates an example of the location of each unit in the rotary frame 15 according to the first embodiment. FIG. 3 illustrates the gantry 10 when it is seen from the front side. Furthermore, it is assumed that the rotary frame 15 is being stopped.

FIG. 3 illustrates the X-ray tube 12a and the X-ray detector 13 within the rotary frame 15. Here, the X-ray tube 12a and the X-ray detector 13 are located in the opposing positions. Furthermore, as illustrated in FIG. 3, an oil cooler 18 is provided within the rotary frame 15. The oil cooler 18 is located near the X-ray tube 12a in a lower section of the rotary frame 15. Specifically, when the gantry 10 is seen from the front side, the oil cooler 18 is located near the lower side of the X-ray tube 12a that is located on the right side.

Furthermore, in the case illustrated in FIG. 3, when the gantry 10 is seen from the front side, the X-ray tube 12a is located on the right side, and the X-ray detector 13 is located on the left side; however, there is no limitation on the embodiment. For example, when the gantry 10 is seen from the front side, the X-ray tube 12a may be located on the left side, and the X-ray detector 13 may be located on the right side. In this case, when the gantry 10 is seen from the front side, the oil cooler 18 is located near the lower side of the X-ray tube 12a that is located on the left side. The oil cooler 18 is also referred to as a "heat radiator".

Furthermore, as illustrated in FIG. 3, after air is drawn into the rotary frame 15 through the air inlet 17a and the air inlet 17b, it flows from the upper section of the rotary frame 15 to the lower section thereof in accordance with the rotation of the fans 19. Then, the fans 19 cause the air, which flows from the upper section of the rotary frame 15, to be discharged out of the gantry 10 through an air outlet 40a and an air outlet 40b. As described above, in the gantry 10 according to the first embodiment, after air is drawn from above the gantry 10, it is taken into the inside of the gantry 10, flows to the lower section thereof, and is discharged through the air outlet 40a and the air outlet 40b. Here, the fan 19 discharges air toward the rail 50. If the air outlet 40a and the air outlet 40b are not distinguished from each other, they are sometimes referred to as the air outlet 40.

Figure 4:
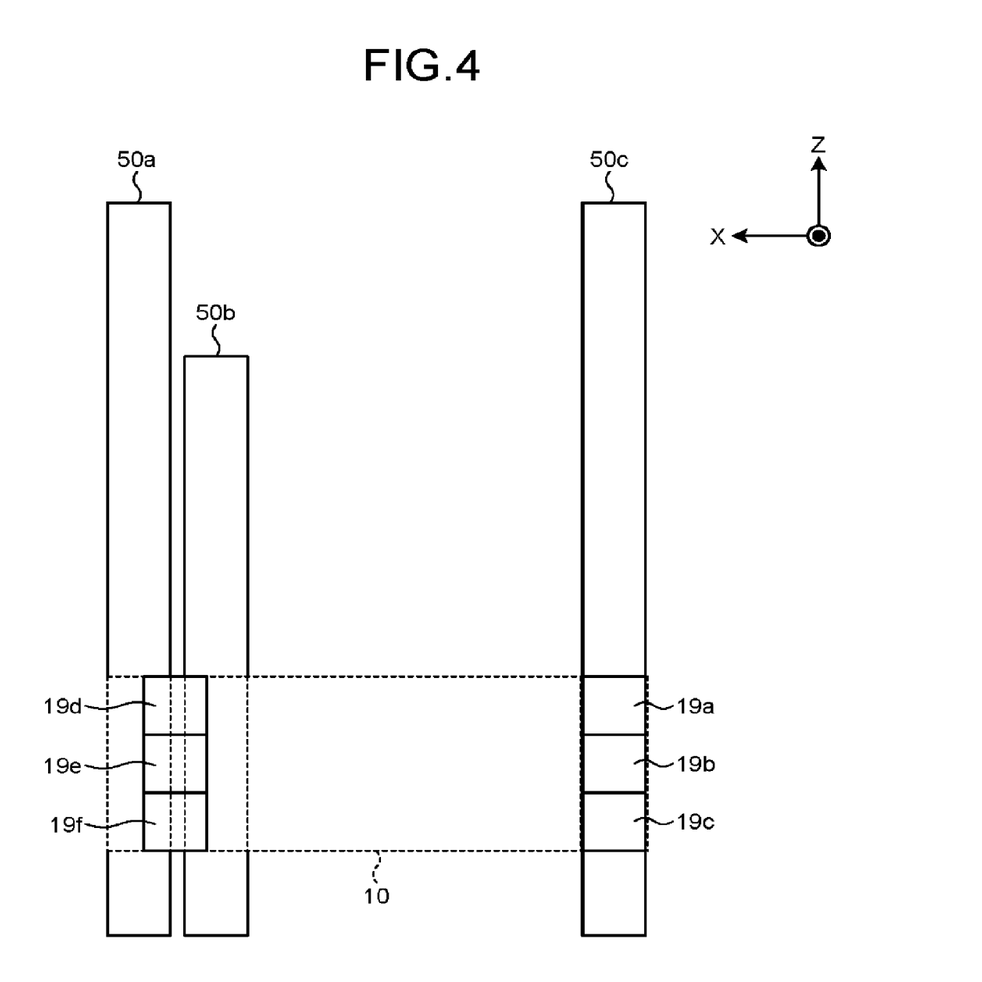
FIG. 4 is a diagram that illustrates the location of fans according to the first embodiment.

FIG. 4 is a diagram that illustrates the location of the fans 19 according to the first embodiment. FIG. 4 illustrates the positional relationship between the rail 50 and the fan 19 when the gantry 10 is seen from the side of the ceiling. Furthermore, in FIG. 4, the gantry 10 is illustrated by a dotted line, and the fans 19 and the rails 50 are illustrated by a solid line.

As illustrated in FIG. 4, in the gantry 10, the fans 19a to 19c are provided at the position that overlaps with the rail 50c. Thus, the fans 19a to 19c discharge air toward the rail 50c. Furthermore, in the gantry 10, the fans 19d to 19f are provided at the position that overlaps with the interval between the rail 50a and the rail 50b. Thus, the fans 19d to 19f discharge air toward the rail 50a and the rail 50b.

Return to FIG. 1. As illustrated in FIG. 1, the rail 50a is covered with a rail cover 90a, the rail 50b is covered with a rail cover 90b, and the rail 50c is covered with a rail cover 90c. If the rail cover 90a, the rail cover 90b, and the rail cover 90c are not distinguished from one another, they are referred to as a rail cover 90. Furthermore, in FIG. 1, in order to illustrate the rail 50, part of the rail cover 90 is eliminated from the illustration.

The rail cover 90a and the rail cover 90b described above are made of a material, such as polyurethane. Furthermore, assume that the surfaces of the rail cover 90a and the rail cover 90b on the side of the rails 50 are the back surfaces, it is preferable that a reinforcing plate (e.g., a reinforcing rib) of, for example, SCM435 (chrome molybdenum steel) is attached to the back surfaces of the rail cover 90a and the rail cover 90b to ensure the strength. With the reinforcing plate, an operator can move on the rail cover 90 that is in contact with the floor surface.

Here, the rail cover 90 that covers the rail 50 through which the gantry 10 is not moving is the same level as the floor surface. As described above, the rail cover 90 of the rail 50 through which the gantry 10 is not moving is the same level as the floor surface; therefore, it is possible to prevent an operator from stumbling or falling. Furthermore, the rail cover 90 of the rail 50 through which the gantry 10 is moving is retracted into the gantry 10. More specifically, when the gantry 10 moves on the rail 50, a movement base 100 that is not illustrated in FIG. 1 moves under the rail cover 90 that is retracted from under the gantry 10.

Figure 5:
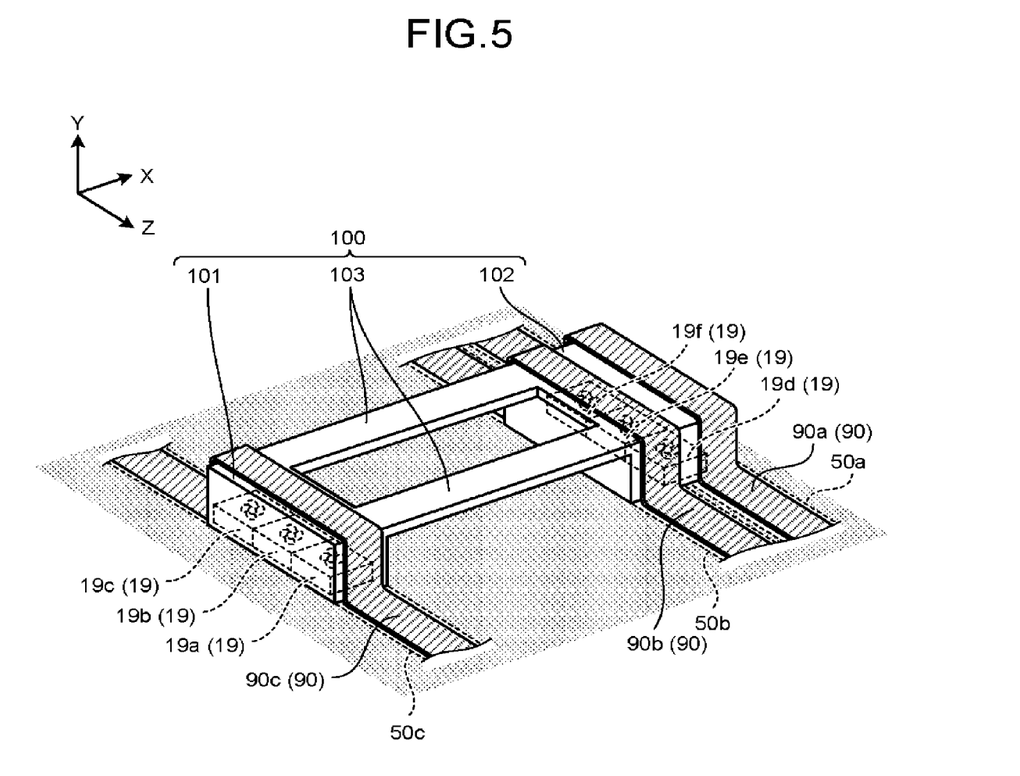
FIG. 5 is a perspective view that illustrates a movement base according to the first embodiment.

With reference to FIG. 5, an explanation is given of the details of the movement base 100. FIG. 5 is a perspective view that illustrates the movement base 100 according to the first embodiment. The illustration of the gantry 10 is omitted from FIG. 5. As illustrated in FIG. 5, the movement base 100 includes a housing section 101, a housing section 102, and a connecting section 103. The inside of the housing section 101 is provided with the space for housing the fans 19, and the fans 19 are housed in the space. Furthermore, the inside of the housing section 102 is provided with the space for housing the fans 19, and the fans 19 are housed in the space. The connecting section 103 connects the housing section 101 and the housing section 102.

Furthermore, as illustrated in FIG. 5, the rail cover 90c is attached to the housing section 101, and the rail cover 90a and the rail cover 90b are attached to the housing section 102. Furthermore, the above-described rail covers 90 are moved on the movement base 100 in accordance with the movement of the gantry 10 on the rails 50. Furthermore, when the gantry 10 moves on the rails 50, the fans 19 are housed in the housing section 101 and the housing section 102; therefore, it is possible to prevent the rail covers 90 from interfering with the fans 19. Furthermore, air outlets are provided on the side surfaces of the housing section 101 and the housing section 102 on the side toward the negative Y-axis direction.

As described above, in the gantry 10 according to the first embodiment, the fans 19 are provided on the bottom section of the gantry 10 so that an air flow is created such that air that is drawn through the top of the gantry 10 flows downward from the upper section of the gantry 10. In this case, for example, air is discharged through an end of the rail 50 or an air outlet that connects from an end of the rail 50 to outside. Thus, according to the first embodiment, it is possible to discharge air toward the rail 50.

Here, according to the first embodiment, in the gantry 10, after the power of the gantry 10 is turned on, the fan 19 serves as an exhaust fan. Thus, for example, during capturing, the fan 19 is operating. As a result, while the power of the gantry 10 is on, air always flows from the upper section to the lower section. Specifically, in the gantry 10 according to the first embodiment, while the power is on, air is continuously discharged from the lower section of the gantry 10. Furthermore, as air flows from the upper section to the lower section, the X-ray tube 12a can be cooled down.

Furthermore, while a doctor performs an operation, there is a possibility that bloods of the subject P or liquid substances used during an operation fall on the floor surface. Here, there is a possibility that bloods of the subject P or liquid substances used during an operation fall on the rail 50. In such a case, according to the first embodiment, air is discharged to the side of the rail 50; therefore, as air is discharged through the rail, even if there is a space between the rail 50 and the floor to flow water, there is a structure to blow air from it; thus, it is possible to prevent inflow of water.

Furthermore, according to the first embodiment, if water flows into the rail 50, the water can be rejected or vaporized due to the same effect as that of a dryer; thus, the effect on a driving mechanism can be reduced. Furthermore, according to the first embodiment, it is possible to facilitate cleaning of the rail 50 through which the X-ray CT apparatus moves. As a result, an improvement is expected from a hygiene perspective. Furthermore, while the power of the gantry 10 is on, the gantry 10 can prevent inflow of water regardless of whether it is during capturing or not during capturing. Furthermore, in the gantry 10, while the power of the gantry 10 is on, if water flows into the rail 50, the water can be rejected or vaporized due to the same effect as that of a dryer regardless of whether it is during capturing or not during capturing.

Furthermore, when the rotary frame 15 is stopped, the X-ray CT apparatus according to the first embodiment performs a control such that the oil cooler 18 is located in a lower section of the rotary frame 15. As a result, when the rotary frame 15 is stopped, the oil cooler 18 is located near the X-ray tube 12a in a lower section of the rotary frame 15. Specifically, in the X-ray CT apparatus according to the first embodiment, the oil cooler 18, which is a heat source, is not located near an air inlet 17 but it is located at a position near an air outlet. In other words, the oil cooler 18 is located on a flow path of air from the air inlet 17 to the air outlet 40 in the rotary frame 15 that is being stopped. Thus, it is possible to prevent air that is drawn from the top of the gantry 10 from being heated after cooling down the oil cooler 18 and the heated air from flowing within the rotary frame 15. As a result, it is possible to efficiently cool the inside of the rotary frame 15.

(Second Embodiment)

Figure 6:
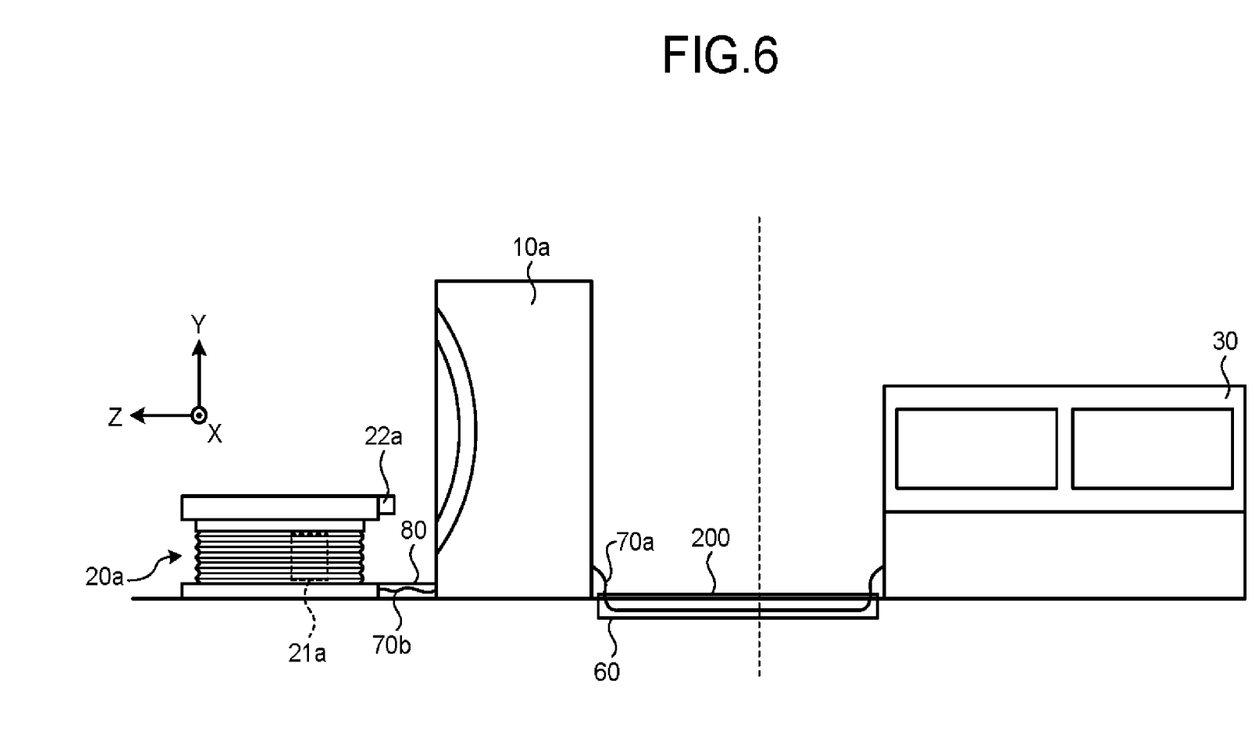
FIG. 6 is a diagram that illustrates an example of the configuration of an X-ray CT apparatus according to a second embodiment.

In the first embodiment, an explanation is given of a case where the X-ray CT apparatus is self-propelling; however, there is no limitation on the embodiment. For example, the X-ray CT apparatus may be a fixed type so that it is attached to the floor surface. FIG. 6 is a diagram that illustrates an example of the configuration of an X-ray CT apparatus according to a second embodiment.

As illustrated in FIG. 6, the X-ray CT apparatus according to the second embodiment includes a gantry 10a, a bed 20a, and the console 30a. The same components of the X-ray CT apparatus according to the second embodiment as those of the X-ray CT apparatus according to the first embodiment are denoted by the same reference numerals, and the detailed explanations are omitted. Furthermore, the orthogonal coordinate system that is formed by the X axis, the Y axis, and the Z axis is defined as illustrated in FIG. 6. Specifically, the X axis indicates a horizontal direction, the Y axis indicates a vertical direction, and the Z axis indicates a direction of the body axis. In the orthogonal coordinate system, the direction indicated by an arrow is a positive direction.

The gantry 10a emits X-rays to the subject P and acquires projection data from detection data on X-rays that are transmitted through the subject P. The gantry 10a is fixedly installed on the floor surface. In other words, the gantry 10a does not move on the rail 50 unlike the gantry 10 according to the first embodiment. Therefore, the functional configuration of the gantry 10a is the same as that of the gantry 10 according to the first embodiment except that the position of an air outlet is different as described later. The bed 20a is the device on which the subject P is placed, and it includes a top board 22a and a bed driving device 21a. The top board 22a is the board on which the subject P is placed. The bed driving device 21a is capable of moving the top board 22a in a direction of the X axis, in a direction of the Y axis, and in a direction of the Z axis under the control of the scan control unit 33 that is included in the console 30a. The console 30a receives an operation on the X-ray CT apparatus by an operator and also reconstructs CT image data from projection data that is acquired by the gantry 10a. The functional configuration of the console 30a is the same as that of the console 30 according to the first embodiment except that the scan control unit 33 does not control the driving mechanism of the rail 50b. Furthermore, the gantry 10a and the bed 20a are installed within a radiation controlled area, and the console 30a is installed outside a radiation controlled area that is partitioned by using an enclosure, such as a wall, that is indicated by a dotted line in FIG. 6.

The above-described X-ray CT apparatus is provided with a transmission mechanism for information that is transmitted and received between the gantry 10a and the other devices, such as the bed 20a or the console 30a. For example, as illustrated in FIG. 6, the gantry 10a is connected to the console 30a via a connection line 70a, and the gantry 10a is connected to the bed 20a via a connection line 70b. With the connection line 70a, information can be transmitted and received between the gantry 10a and the console 30a and, with the connection line 70b, information can be transmitted and received between the gantry 10a and the bed 20a. Furthermore, the transmission mechanism is sometimes connected via a relay point. For example, if the distance between the gantry 10a and the console 30a is long, the connection line 70a is not a single cable, but it is formed by connecting multiple cables via a relay point.

Furthermore, it is preferable that there are no obstacles, or the like, on the floor surface of an examination room and an operator, engineer, or the like, is able to walk freely. Therefore, a transmission path that houses the transmission mechanism is provided in an examination room. The transmission path is the path that houses a controller that controls the gantry 10a.

For example, as illustrated in FIG. 6, a groove 60 is provided under the floor surface as a transmission path that houses the connection line 70a. Furthermore, the groove 60 is covered with a cover 200. The cover 200 is removably fitted into the groove 60, and it may be formed with a material that ensures the strength such that an operator, engineer, or the like, can walk. This allows an operator, engineer, or the like, to move on the cover 200 that is in contact with the floor surface. Furthermore, as illustrated in FIG. 6, the connection line 70b is provided on the floor surface. The connection line 70b is covered with a protection member 80. The protection member 80 is formed with a material, for example, polyurethane. Furthermore, assume that the surface of the protection member 80 on the side of the connection line 70b is the back surface, it is preferable that a reinforcing plate (e.g., a reinforcing rib) of, for example, SCM435 (chrome molybdenum steel) is attached to the back surface of the protection member 80 to ensure the strength. With the reinforcing plate, an operator can move on the protection member 80 that is in contact with the floor surface. Thus, there are no obstacles, or the like, on the floor surface of an examination room where the gantry 10a and the bed 20a are installed, and an operator, engineer, or the like, can walk freely.

Figure 7:
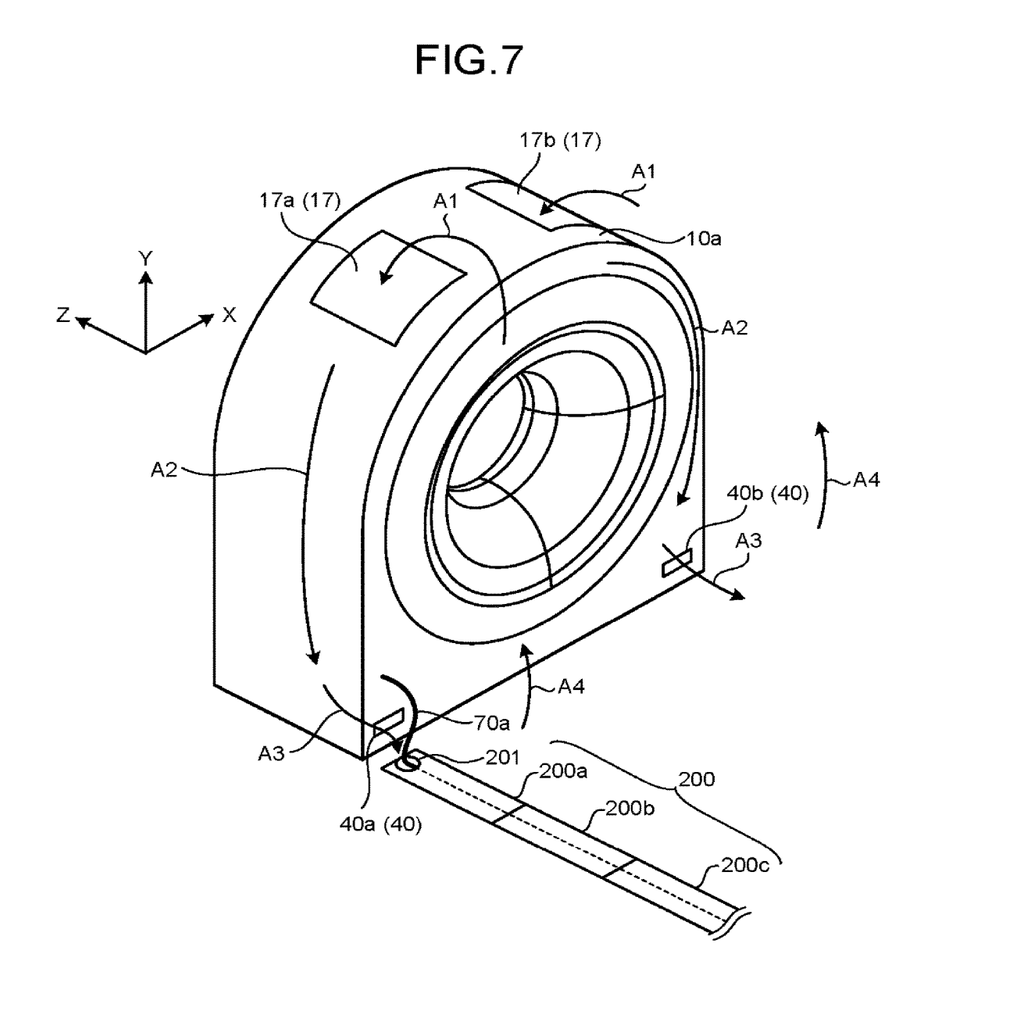
FIG. 7 is a perspective view that illustrates a gantry according to the second embodiment.

Furthermore, there is sometimes a gap in the cover 200 that covers the groove 60. FIG. 7 is a perspective view that illustrates the gantry 10a according to the second embodiment. As illustrated in FIG. 7, the connection line 70a that connects the gantry 10a and the console 30a is pulled out of the gantry 10a and is inserted into the groove 60 through a through-hole 201 that is formed on the cover 200. Furthermore, the connection line 70a reaches the console 30a via the groove 60. FIG. 7 illustrates the gantry 10a and the cover 200 that covers the groove 60 that is a transmission path. For example, it is preferable that, if the connection line 70a is faulty, maintenance is promptly conducted. Therefore, the cover 200 is formed with multiple members so that it is possible to easily access the faulty connection line 70a during maintenance. For example, as illustrated in FIG. 7, the cover 200 is formed with a cover member 200a, a cover member 200b, and a cover member 200c.

However, as the cover 200 is formed with multiple members, there is a little gap. For example, there is sometimes a gap between the cover member 200a and the cover member 200b or between the cover member 200b and the cover member 200c. Furthermore, as each cover member is removably fitted into the groove 60, there is sometimes a gap between each cover member and the groove 60. There is a possibility that liquids, such as water that is generated during an operation or bloods of a subject, enter the groove 60 via the above-described gap. As described above, the connection line 70a is sometimes formed by connecting multiple cables via a relay point and, to protect the relay point, it is preferable to prevent liquids from entering the groove 60.

As described above, in the X-ray CT apparatus according to the second embodiment, air within the gantry 10a is discharged through the transmission path that houses the transmission mechanism. For example, as illustrated in FIG. 7, the X-ray CT apparatus according to the second embodiment includes the air inlet 17a, the air inlet 17b, the air outlet 40a, and the air outlet 40b. If the air inlet 17a and the air inlet 17b are not distinguished from each other, they are sometimes referred to as the air inlet 17 and, if the air outlet 40a and the air outlet 40b are not distinguished from each other, they are sometimes referred to as the air outlet 40. The air inlet 17 is provided on the gantry 10a so that air is drawn into the gantry 10a from outside the gantry 10a. The air outlet 40 is provided in a lower section of the gantry 10a, and air within the gantry 10a is discharged through a path that houses the controller that controls the gantry 10a. Furthermore, the undepicted fans 19 are provided near the air outlet 40a and the air outlet 40b in the lower section of the gantry 10a. Thus, in the gantry 10a, the air flow illustrated in FIG. 7 is formed.

For example, air is drawn into the rotary frame 15 through the air inlet 17a and the air inlet 17b (see A1). Then, when the fans 19 are rotated, the air that is drawn into the rotary frame 15 flows from an upper section of the rotary frame 15 to a lower section thereof (see A2). For example, the air flowing from the upper section of the rotary frame 15 is discharged out of the gantry 10a by the fans 19 through the air outlet 40a and the air outlet 40b (see A3). Here, the air outlet 40 is located near the transmission path of the transmission mechanism in the lower section of the gantry 10a. Therefore, part of air that is discharged out of the gantry 10a is taken into the groove 60 through the through-hole 201 that is provided on the cover 200. Specifically, in the X-ray CT apparatus according to the second embodiment, air within the gantry 10a is discharged through the transmission path that houses the transmission mechanism. Air that is discharged out of the gantry 10a and that is not taken into the groove 60 is again drawn into the rotary frame through the air inlet 17a and the air inlet 17b (see A4).

As described above, in the X-ray CT apparatus according to the second embodiment, air within the gantry 10a is discharged through the transmission path that houses the transmission mechanism. Thus, even if there is a gap between the cover 200 and the floor to flow water, as there is a structure to blow air from it, inflow of water can be prevented. Furthermore, according to the second embodiment, even if water flows into the groove 60, water can be rejected or vaporized due to the same effect as that of a dryer. As a result, if the transmission path houses the transmission mechanism in which multiple cables are connected via a relay point, the relay point can be protected.

Furthermore, a relay device (board) that controls transaction of signals with multiple X-ray CT apparatuss may be provided on the transmission path that is provided on the floor surface. For example, if multiple X-ray CT apparatuss are controlled by a single console, a relay device is connected to a signal line for controlling transaction of signals between the console 30a and a different X-ray CT apparatus that is installed in a different room. Alternatively, if an X-ray CT apparatus and an X-ray diagnostic apparatus are controlled by a single console, for example, a relay device is connected to a signal line for controlling transaction of signals between the console 30a and the X-ray diagnostic apparatus that is installed in the same space as the X-ray CT apparatus. The relay device is, for example, an electronic circuit, such as a Central Processing Unit (CPU) or a Micro Processing Unit (MPU), or an integrated circuit, such as an Application Specific Integrated Circuit (ASIC) or a Field Programmable Gate Array (FPGA). As described above, in the X-ray CT apparatus according to the second embodiment, if a relay device is installed in the transmission path, the relay device can be protected from liquids.

Furthermore, a duct may be provided on the air outlet 40 so that air that is discharged through the air outlet 40 is effectively taken into the transmission path. Moreover, the angle of the fan 19 relative to the floor surface can be appropriately changed so that air that is discharged through the air outlet 40 is effectively taken into the transmission path.

Furthermore, in the example illustrated in FIGS. 6 and 7, an explanation is given of a case where the connection line 70a is temporarily pulled out of the gantry 10a and is then inserted into the groove 60 through the through-hole 201 that is formed on the cover 200; however, there is no limitation on the embodiment. For example, the connection line 70*a* may be inserted into the groove 60 through the bottom surface of the gantry 10*a*. In such a case, the air outlet 40 and the fan 19 are provided on the bottom surface of the gantry 10*a* as is the case with the gantry 10 according to the first embodiment.

Furthermore, in the example illustrated in FIGS. 6 and 7, an explanation is given of a case where the air outlet 40 is provided on the side of the transmission path that houses the connection line 70*a*; however, there is no limitation on the embodiment. For example, the air outlet 40 may be provided on the side of the transmission path that houses the connection line 70*b*. Thus, if liquids drop in the interval between the gantry 10*a* and the bed 20*a*, liquids can be rejected or vaporized.

(Other Embodiments)

Embodiments are not limited to the above-described embodiments.

Air that is discharged from the gantry 10 (10*a*) through a path that houses a controller that controls the gantry 10 (10*a*) may be discharged out of an examination room. For example, air that is discharged from the gantry 10 through a movement path that houses the driving mechanism that moves the gantry 10 may be discharged out of an examination room. Furthermore, air that is discharged from the gantry 10*a* through a path that houses the transmission mechanism of information that is transmitted and received between the gantry 10*a* and the bed 20*a* may be discharged out of an examination room. Furthermore, air that is discharged from the gantry 10*a* through a path that houses the transmission mechanism of information that is transmitted and received between the gantry 10*a* and the console 30*a* may be discharged into the space where the console 30*a* is installed. Furthermore, air that is discharged through a path that houses the controller that controls the gantry 10 (10*a*) may be circulated to the air inlet 17 through a duct, or the like. Thus, it is possible to prevent the discharged air from flowing within an examination room, and it is possible to maintain the clean state of the examination room.

Furthermore, in the above-described embodiment, an explanation is given of a case where the air inlet 17 is provided in an upper section of the gantry 10 (10*a*); however, there is no limitation on the embodiment. For example, the air inlet 17 may be provided below the central position in a height direction of the gantry 10 (10*a*). Furthermore, in such a case, air that is drawn through the air inlet 17 is temporarily passed through an upper section of the gantry 10 (10*a*) via, for example, a duct and is discharged through the air outlet 40 that is provided in a lower section of the gantry 10 (10*a*), whereby the X-ray tube 12*a* can be cooled down.

Furthermore, the air inlet 17 may be provided below the air outlet 40. In this case, air that is drawn through the air inlet 17 is circulated within the gantry 10 (10*a*) through, for example, a duct and is discharged through the air outlet 40.

Furthermore, the air inlet 17 may be provided, for example, in an upper section of the gantry 10 (10*a*) and in a lower section of the gantry 10 (10*a*). In this case, after the power of the X-ray CT apparatus is turned on, air is always drawn through the air inlet 17 in the upper section and is discharged through the air outlet 40. Thus, the X-ray tube 12*a* can be always cooled down. Furthermore, during capturing, air is drawn through the air inlet 17 that is provided in the lower section in addition to the air inlet 17 in the upper section. Therefore, the amount of air that is discharged through the path that houses the controller that controls the gantry 10 (10*a*) is increased; thus, it is possible to prevent the inflow of water or to reject or vaporize water more effectively.

Furthermore, in the above-described embodiment, an explanation is given of a case where the fans 19 are provided in the lower section on the right and left sides of the gantry 10; however, there is no limitation on the embodiment. For example, the fans 19 may be provided on any one of the right and left sides of the gantry 10. More specifically, the gantry 10 may not include the fans 19*d* to 19*f* that are illustrated in FIG. 4, and the fans 19*a* to 19*c* may be provided at the position that overlaps with the rail 50*c*. Alternatively, the gantry 10 may not include the fans 19*a* to 19*c* that are illustrated in FIG. 4, and the fans 19*d* to 19*f* may be provided only at the position that overlaps with the interval between the rail 50*a* and the rail 50*b*.

Furthermore, in the above-described embodiment, an explanation is given of a case where the fans 19*a* to 19*c* are provided at the position that overlaps with the rail 50*c* and the fans 19*d* to 19*f* are provided at the position that overlaps with the interval between the rail 50*a* and the rail 50*b*; however, there is no limitation on the embodiment. For example, the fans 19*a* to 19*c* may be provided at the position that overlaps with the rail 50*c*, the fans 19*d* to 19*f* may be provided at the position that overlaps with the rail 50*b*, and fans 19*g* to 19*i* may be provided at the position that overlaps with the rail 50*a*.

Furthermore, in the above-described embodiment, an explanation is given of a case where the fan 19 that serves as an exhaust fan is provided in the lower section of the gantry 10; however, there is no limitation on the embodiment. For example, a fan that serves as an air supply fan may be provided in an upper section of the gantry 10. In such a case, a fan that is provided in an upper section of the gantry 10 is located near the air inlet 17*a* so as to draw air into the rotary frame 15 from outside the gantry 10. Alternatively, for example, a fan that serves as an air supply fan may be provided in an upper section of the gantry 10, and the fan 19 that serves as an exhaust fan may be provided in a lower section of the gantry 10. Furthermore, if a fan that serves as an air supply fan is provided in an upper section of the gantry 10, the number of air supply fans may be optionally changed. Moreover, if the fan 19 that serves as an exhaust fan is provided in a lower section of the gantry 10, the number of exhaust fans may be optionally changed.

Furthermore, in the above-described embodiment, an explanation is given of a case where the oil cooler 18 is used as a heat radiator; however, there is no limitation on the embodiment. For example, the gantry 10 may use a heat radiator other than the oil cooler 18 to cool down the X-ray tube 12*a*. Furthermore, the gantry 10 may not use a heat radiator if it is ensured that the X-ray tube 12*a* can be cooled down.

Furthermore, in the above-described embodiment, an explanation is given of a case where, after the power of the X-ray CT apparatus is turned on before the start of an examination, the power-on state is maintained all day in principle; however, there is no limitation on the embodiment. For example, the power of the X-ray CT apparatus may be turn on and off for each examination.

Furthermore, a power source that supplies electric power to the fan 19 and a power source that supplies electric power to the gantry 10 (10*a*) may be provided separately. In this case, even if the power of the gantry 10 (10*a*) is off, the fan 19 can be continuously operating, and air can be discharged from the lower section of the gantry 10 (10*a*). On and off control of the power supply to the fan 19 can be controlled by the scan control unit 33.

In the above-described embodiment, an explanation is given of a case where the rail 50 is covered with the rail cover 90; however, there is no limitation on the embodiment. For example, the rail 50 may not be covered with the rail cover 90.

Furthermore, in the above-described embodiment, an explanation is given of a case where the gantry 10 is moved by using the three rails, i.e., the rail 50*a*, the rail 50*b*, and the rail 50*c*; however, there is no limitation on the number of rails that are used for moving the gantry 10. For example, the gantry 10 may be moved by using two rails or may be moved by using four rails. In this case, the fan 19 discharges air toward a rail.

Furthermore, in the above-described embodiment, an explanation is given of a case where the gantry 10 moves on the rail 50; however, there is no limitation on the embodiment. For example, it is applicable to a case where the gantry 10 moves on other than the rail. Furthermore, it is applicable to a case where the gantry 10 is not self-propelled. More specifically, the gantry 10 may be fixed to the floor surface. In this case, if air is discharged from a lower section of the gantry, for example, dust or water that is accumulated in the lower section of the gantry 10 can be discharged.

Figure 8:
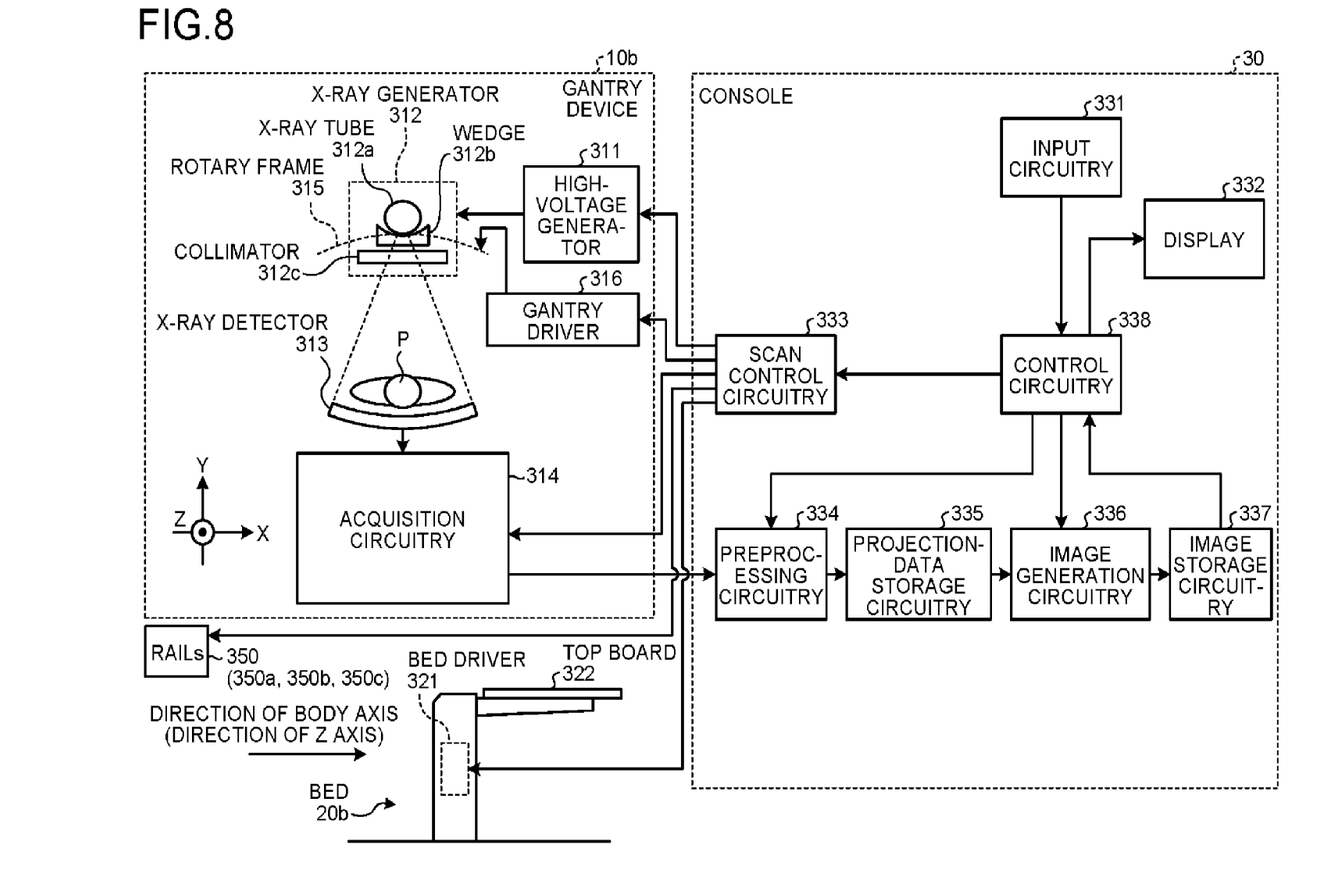
FIG. 8 is a diagram that illustrates an example of the configuration of an X-ray CT apparatus according to another embodiment.

The X-ray CT apparatus illustrated in the description of the first embodiment and the second embodiment may be configured as illustrated in FIG. 8, for example. FIG. 8 is a diagram that illustrates an example of the configuration of an X-ray CT apparatus according to another embodiment.

As illustrated in FIG. 8, the X-ray CT apparatus according to the other embodiment includes a gantry 10*b*, a bed 20*b*, the console 30*b*, and rails 350 (350*a*, 350*b*, 350*c*). The gantry 10*b*, the bed 20*b*, the console 30*b*, and the rails 350 (350*a*, 350*b*, 350*c*) correspond to the gantry 10, the bed 20, the console 30, and the rails 50 (50*a*, 50*b*, 50*c*) illustrated in FIG. 2, respectively.

As illustrated in FIG. 8, the gantry 10*b* includes a high voltage generator 311, an X-ray generator 312, an X-ray detector 313, acquisition circuitry 314, a rotary frame 315, and a gantry driver 316. The high voltage generator 311, the X-ray generator 312, the X-ray detector 313, the acquisition circuitry 314, the rotary frame 315, and the gantry driver 316 illustrated in FIG. 8 correspond to the X-ray radiation control unit 11, the X-ray generator 12, the X-ray detector 13, the acquisition unit 14, the rotary frame 15, and the gantry driving unit 16 illustrated in FIG. 2, respectively.

As illustrated in FIG. 8, the bed 20*b* includes a top board 322 and a bed driver 321. The top board 322 and the bed driver 321 illustrated in FIG. 8 correspond to the top board 22 and the bed driving device 21 illustrated in FIG. 2, respectively.

As illustrated in FIG. 8, the console 30*b* includes input circuitry 331, display 332, scan control circuitry 333, preprocessing circuitry 334, projection-data storage circuitry 335, image generation circuitry 336, image storage circuitry 337, and control circuitry 338. The input circuitry 331, the display 332, the scan control circuitry 333, the preprocessing circuitry 334, the projection-data storage circuitry 335, the image generation circuitry 336, the image storage circuitry 337, and the control circuitry 338 illustrated in FIG. 8 correspond to the input device 31, the display device 32, the scan control unit 33, the preprocessing unit 34, the projection-data storage unit 35, the image generation unit 36, the image storage unit 37, and the control unit 38 illustrated in FIG. 2, respectively.

The components illustrated in FIG. 8 may be integrated into one processor that implements the respective functions. The term "processor" used in the above description means, for example, a central preprocess unit (CPU) and a graphics processing unit (GPU), or circuitry such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in storage circuitry. Instead of being stored in storage circuitry, the program may be built directly in circuitry of the processor. In this case, the processor implements a function by loading and executing the program built in the circuitry. The processors in the present embodiment are not limited to a case in which each of the processors is configured as a single circuit. A plurality of separate circuits may be combined as one processor that implements the respective functions.

According to at least one of the above-described embodiments, air can be discharged from a lower section of the gantry.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An X-ray CT apparatus, comprising:
a gantry configured to support an X-ray tube and an X-ray detector;
an air inlet configured to be provided in the gantry to draw air into the gantry from outside the gantry; and
an air outlet configured to discharge air from the gantry to a movement path provided outside of the gantry, wherein a driving mechanism that moves the gantry is included within the movement path.
2. The X-ray CT apparatus according to claim 1, wherein the air outlet is provided on at least any one of movement paths through which the gantry moves.
3. An X-ray CT apparatus, comprising:
a gantry configured to support an X-ray tube and an X-ray detector;
an air inlet configured to be provided in the gantry to draw air into the gantry from outside the gantry; and
an air outlet configured to discharge air from the gantry to a transmission path provided outside the gantry, wherein
a transmission mechanism of information that is transmitted and received between the gantry and a console is included within the transmission path.
4. The X-ray CT apparatus according to claim 3, wherein the air outlet is provided adjacent to the transmission path of the transmission mechanism.
5. The X-ray CT apparatus according to claim 1, wherein the gantry supports a rotary frame that houses the X-ray tube and the X-ray detector, and
a heat radiator is provided to release heat that is generated by the X-ray tube, the heat radiator being provided in a portion of the rotary frame.

6. The X-ray CT apparatus according to claim 5, wherein the heat radiator is provided adjacent to the X-ray tube.

7. The X-ray CT apparatus according to claim 5, wherein the rotary frame is controlled to be stopped so that the heat radiator is provided on a flow path of air from the air inlet to the air outlet in the rotary frame.

8. The X-ray CT apparatus according to claim 6, wherein the rotary frame is controlled to be stopped so that the heat radiator is provided on a flow path of air from the air inlet to the air outlet in the rotary frame.

9. An X-ray CT apparatus, comprising:
a gantry configured to support an X-ray tube and an X-ray detector;
an air inlet configured to be provided in the gantry to draw air into the gantry from outside the gantry; and
an air outlet configured to discharge air from the gantry to a transmission path provided outside the gantry, wherein
a transmission mechanism of information that is transmitted from the gantry to a bed is included within the transmission path.

10. The X-ray CT apparatus according to claim 9, wherein the air outlet is provided adjacent to the transmission path of the transmission mechanism.

11. The X-ray CT apparatus according to claim 3, wherein the gantry supports a rotary frame that houses the X-ray tube and the X-ray detector, and
a heat radiator is provided to release heat that is generated by the X-ray tube, the heat radiator being provided in a portion of the rotary frame.

12. The X-ray CT apparatus according to claim 11, wherein the heat radiator is provided adjacent to the X-ray tube.

13. The X-ray CT apparatus according to claim 11, wherein the rotary frame is controlled to be stopped so that the heat radiator is provided on a flow path of air from the air inlet to the air outlet in the rotary frame.

14. The X-ray CT apparatus according to claim 12, wherein the rotary frame is controller, to be stopped so that the heat radiator is provided on a flow path of air from the air inlet to the air outlet in the rotary frame.

15. The X-ray CT apparatus according to claim 9, wherein
the gantry supports a rotary frame that houses the X-ray tube and the X-ray detector, and
a heat radiator is provided to release heat that is generated by the X-ray tube, the heat radiator being provided in a portion of the rotary frame.

16. The X-ray CT apparatus according to claim 15, wherein the heat radiator is provided adjacent to the X-ray tube.

17. The X-ray CT apparatus according to claim 15, wherein the rotary frame is controlled to be stopped so that the heat radiator is provided on a flow path of air from the air inlet to the air outlet in the rotary frame.

18. The X-ray CT apparatus according to claim 16, wherein the rotary frame is controlled to be stopped so that the heat radiator is provided on a flow path of air from the air inlet to the air outlet in the rotary frame.

* * * * *